United States Patent [19]

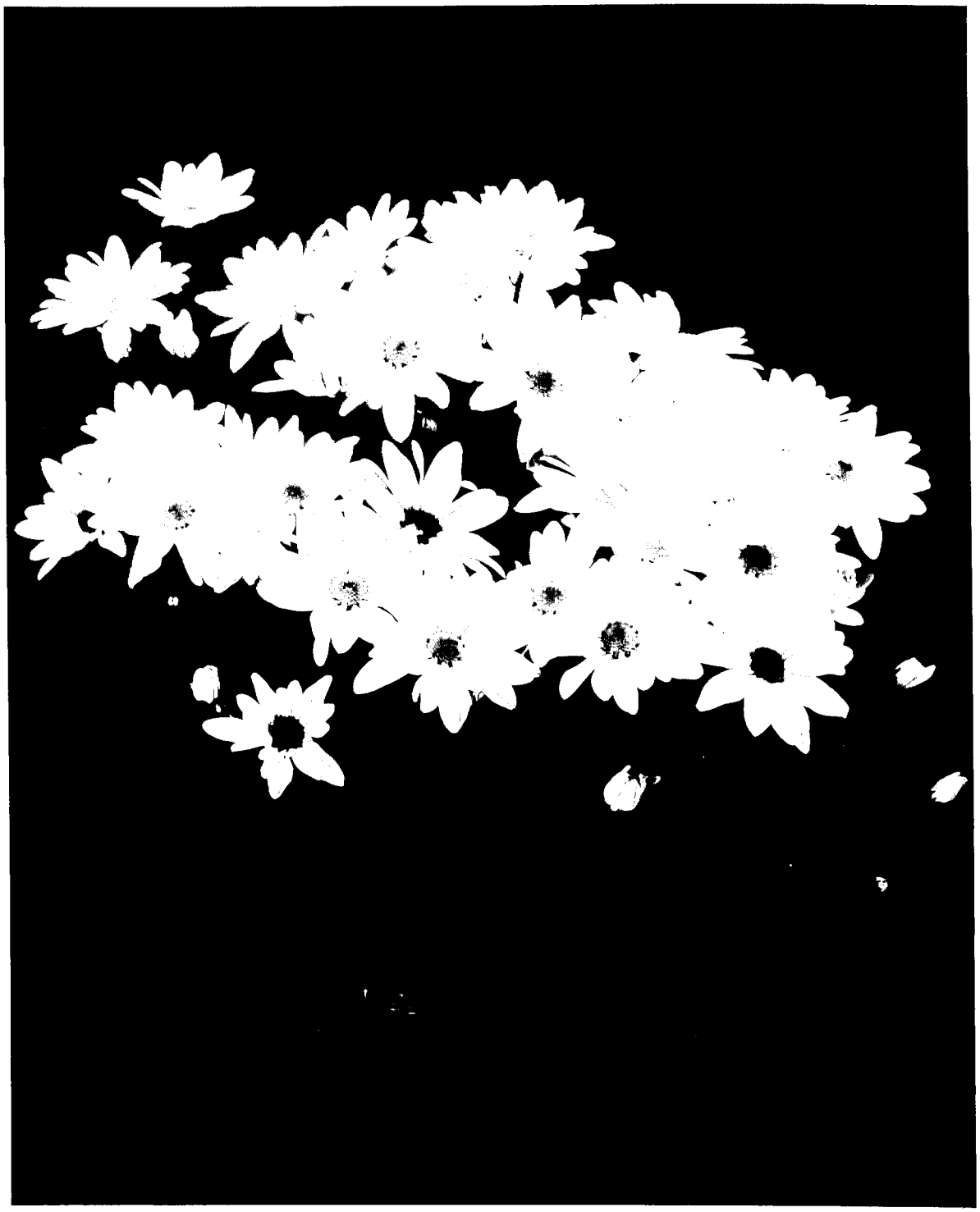

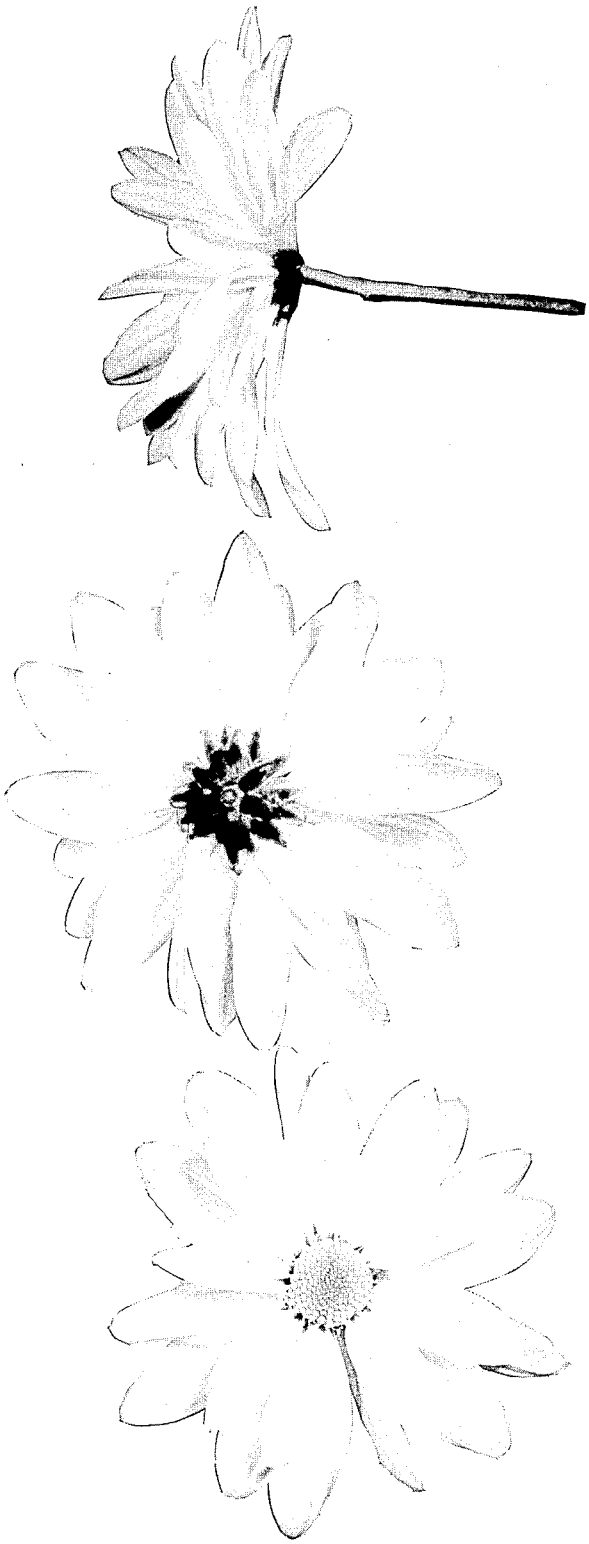

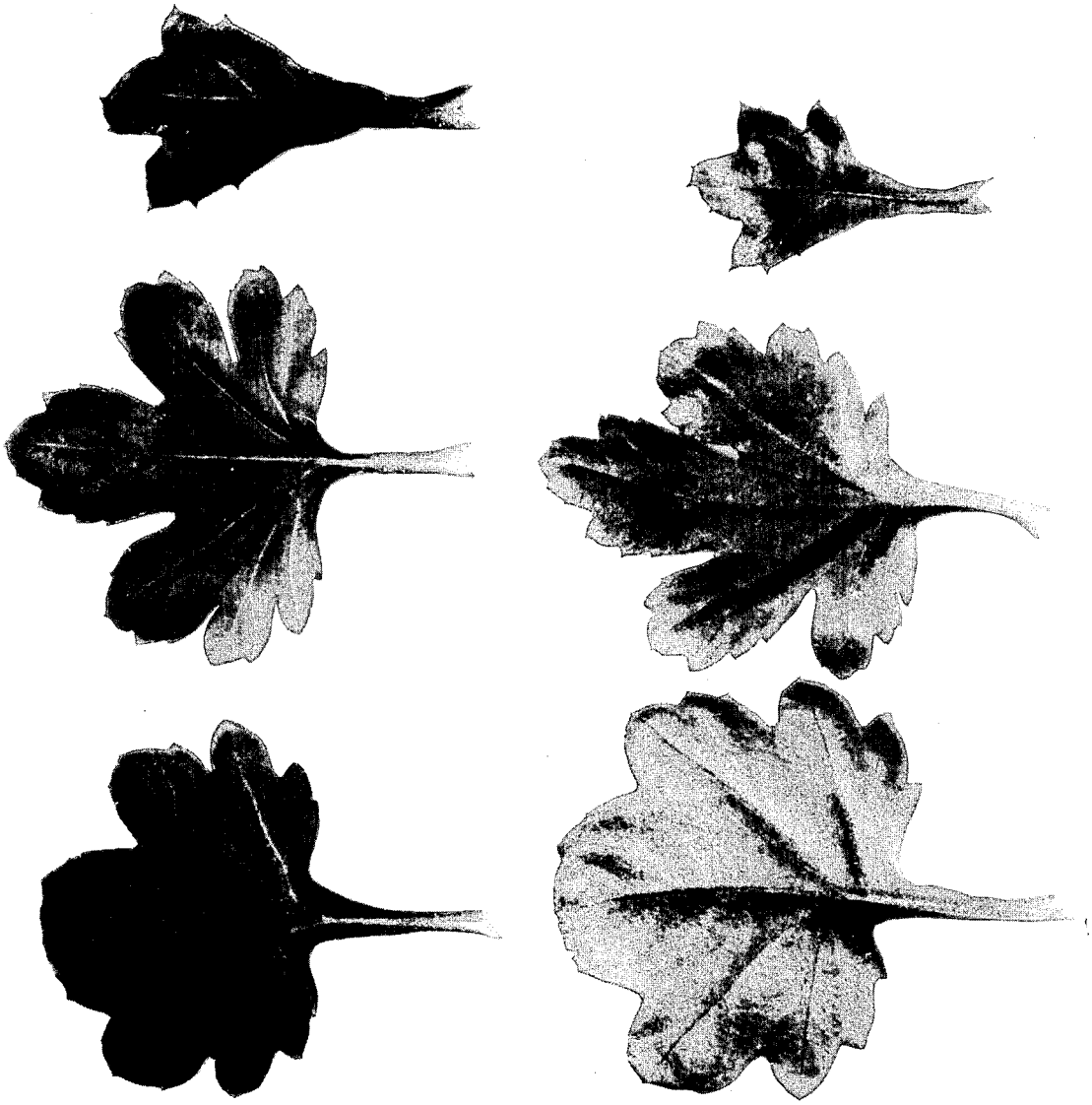

Hellberg

[11] Patent Number: Plant 5,785

[45] Date of Patent: Aug. 19, 1986

[54] CHRYSANTHEMUM PLANT NAMED DARK YELLOW GARLAND

[76] Inventor: Herman Hellberg, 70 E. Hillcrest Ave., Chalfont, Pa. 18914

[21] Appl. No.: 665,923

[22] Filed: Oct. 29, 1984

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A chrysanthemum plant named Dark Yellow Garland characterized as to uniqueness by the combined characteristics of flat capitulum form, daisy capitulum type, dark yellow ray floret color, diameter across face of capitulum ranging from 7 to 9 cm. at maturity, uniform nine week flowering response, tall plant height and upright branching pattern.

3 Drawing Figures

The present invention comprises a new and distinct cultivar of *Chrysanthemum morifolium,* Ramat., named Dark Yellow Garland.

Dark Yellow Garland was discovered and selected on Apr. 18, 1979 by Herman Hellberg in a greenhouse of the Peter Hellberg Company, 332 Main St., Chalfont, Pa. 18914. The parent cultivar was Yellow Garland, disclosed by U.S. Plant Pat. No. 3,671. This sectorial selection of Yellow Garland resulted from spontaneous mutation.

The first act of asexual reproduction of Dark Yellow Garland was accomplished when vegetative cuttings were taken from the initial selection on May 5, 1979 in a controlled environment in Chalfont, Pa. by Herman Hellberg. Horticultural examination of selected units initiated May 29, 1980 has demonstrated that the combination of characteristics as herein disclosed for Dark Yellow Garland are firmly fixed and are retained through successive generations of asexual reproduction.

Dark Yellow Garland has not been observed under all possible environmental conditions. The phenotype may vary significantly with variations in environment such as temperature, light intensity and day length. The observations, measurements and comparisons describe plants grown in Salinas, Calif. under greenhouse conditions which approximate those generally used in commercial practice.

The following traits have been repeatedly observed and are determined to be basic characteristics of Dark Yellow Garland which in combination distinguish this chrysanthemum as a new and distinct cultivar:

(1) Flat capitulum form.

(2) Daisy capitulum type.

(3) Dark yellow ray floret color.

(4) Diameter across face of capitulum ranging from 7 to 9 cm. at maturity.

(5) Uniform nine week photoperiodic flowering response to short days.

(6) Tall plant height, requiring 1 to 2 long day weeks prior to short days followed by a pinch after 7 short days, and 2 to 3 applications of 2500 ppm B-9 SP at intervals of 14, 21 and 28 short days from the pinch to attain a flowered plant height of 25 to 35 cm. in 6" pots.

(7) Upright branching pattern.

The accompanying photographic drawings depict typical leaf and inflorescence characteristics of Dark Yellow Garland. Sheet 1 is a color photograph of a plant of Dark Yellow Garland grown as a pinched spray pot mum, with colors being as accurate as possible with renditions of this type. Sheet 2 is a black and white photograph of three views of the inflorescence of Dark Yellow Garland. Sheet 3 shows the upper surface and under surface of the leaves of Dark Yellow Garland in three stages of development (mature, intermediate and immature).

Of the many commercial cultivars known to the present inventor, the most similar in comparison to Dark Yellow Garland is Yellow Garland, disclosed in U.S. Plant Pat. No. 3,671. Reference is made to attached Chart A which compares certain characteristics of Dark yellow Garland to those same characteristics of Yellow Garland.

All traits of the new and parent cultivar are similar with the exception of color. The color of Dark Yellow Garland is significantly deeper than Yellow Garland at all stages of development, with a slower rate of oxidation. Dark Yellow Garland exhibits 6A and 7A on the upper surface compared to 4A for Yellow Garland. The under surface of Dark Yellow Garland is 5A compared to 4C for Yellow Garland.

In the following description, color references are made to The Royal Horticultural Society Colour Chart. The color values were determined between 2:00 P.M. and 2:30 P.M. on Aug. 2, 1984. under 380 foot-candle light intensity at Salinas, Calif.

Classification:

*Botanical.*—*Chrysanthemum morifolium,* Ramat., cv Dark Yellow Garland.

*Commercial.*—Daisy spray pot mum.

I. Inflorescence:

A. *Capitulum.*—Form: Flat. Type: Daisy. Diameter across face: 7 to 9 cm.

B. *Corolla of ray florets.*—Color (general tonality from a distance of three meters): Dark yellow. Color (upper surface): 6A and 7A. Color (under surface): 5A. Shape: Oblong. Blunt notched tip.

C. *Corolla of disc florets.*—Color (mature): 145A. Color (immature): 1A.

D. *Reproductive organs.*—Androecium: Present disc florets only; scant pollen. Gynoecium: Present both ray and disc florets.

II. Plant:

A. *General appearance.*—Height: Tall; 30 to 38 cm. given 1 to 2 long day weeks prior to pinch and short days and 1 to 2 applications of 2500 ppm B-9 SP, the first at 14, the second at 21 days after the beginning of short days to attain a flowered plant height of 25 to 35 cm. in 6″ pots. Branching pattern: Upright.

B. *Foliage.*—Color (upper surface): 147A. Color (under surface): 147B. Shape: Spatulate lobed. Finely serrated.

CHART A

COMPARISON OF DARK YELLOW GARLAND AND YELLOW GARLAND

| CULTIVAR | RAY FLORET COLOR | CAPITULUM FORM AND TYPE | BRANCHING PATTERN |
|---|---|---|---|
| DARK YELLOW GARLAND | DARK YELLOW UPPER SURFACE 6A, 7A UNDER SURFACE 5A | FLAT DAISY | UPRIGHT |
| YELLOW GARLAND | YELLOW UPPER SURFACE 4A, 4B UNDER SURFACE | FLAT DAISY | UPRIGHT |

CHART A-continued

COMPARISON OF DARK YELLOW GARLAND AND YELLOW GARLAND

| CULTIVAR | DIAMETER ACROSS FACE OF CAPITULUM | PLANT HEIGHT | FLOWERING RESPONSE PERIOD |
|---|---|---|---|
| DARK YELLOW GARLAND | 7 to 9 cm. | TALL 30 to 38 cm. | 9 WEEKS |
| YELLOW GARLAND | 7 to 9 cm. | TALL 30 to 38 cm. | 9 WEEKS |

COMPARISONS MADE OF PLANTS GROWN AS PINCHED SPRAY POT MUMS IN SALINAS, CALIFORNIA

I claim:

1. A new and distinct cultivar of *Chrysanthemum morifolium,* Ramat., plant named Dark Yellow Garland, as described and illustrated, and particularly characterized as to uniqueness by the combined characteristics of flat capitulum form; daisy capitulum type; dark yellow ray floret color; diameter across face of capitulum ranging from 7 to 9 cm. at maturity; uniform nine week flowering response; tall plant height and upright branching pattern.

* * * * *